(12) United States Patent
Otsuki et al.

(10) Patent No.: US 7,718,826 B2
(45) Date of Patent: May 18, 2010

(54) IONIC COMPOUND

(75) Inventors: Masashi Otsuki, Koganei (JP); Hiroshi Kanno, Kodaira (JP)

(73) Assignee: Bridgestone Corporation, Tokyo (JP)

( * ) Notice: Subject to any disclaimer, the term of this patent is extended or adjusted under 35 U.S.C. 154(b) by 161 days.

(21) Appl. No.: 12/092,729

(22) PCT Filed: Oct. 12, 2006

(86) PCT No.: PCT/JP2006/320395

§ 371 (c)(1),
(2), (4) Date: May 29, 2008

(87) PCT Pub. No.: WO2007/055081

PCT Pub. Date: May 18, 2007

(65) Prior Publication Data

US 2008/0269492 A1    Oct. 30, 2008

(30) Foreign Application Priority Data

Nov. 8, 2005   (JP)  ............................. 2005-323558
May 17, 2006   (JP)  ............................. 2006-138081

(51) Int. Cl.
*C07F 9/547* (2006.01)
(52) U.S. Cl. ...................................................... 564/13
(58) Field of Classification Search .................... 564/13
See application file for complete search history.

(56) References Cited

FOREIGN PATENT DOCUMENTS

JP    2004-111294 A    4/2004
JP    2004-146346 A    5/2004

OTHER PUBLICATIONS

V.V. Vapirov et al., "Chemical properties of the reaction products of cyclic phosphonitrile chloride trimer with organic bases", Russian Journal of General Chemistry, (1998) 68(1), compound No. VI, pp. 24-27.
A.E. Shumeiko et al., Salts of hexachlorocyclophosphazotriene with teriary amines, Zhurnal Obshchei Khimii, (1986), 56(10, compound Nos. I, III, pp. 2275-2277.
John N. Rapko et al., "Reactions of trimethyloxonium fluoroborate with alkylamino- and phenyl-substituted cyclotriphosphonitriles", Inorganic Chemistry, (1970), 9 (6), Table I, II, IV, pp. 1401-1405.
Charles D. Schmulbach et al., "Kinetics of pyridine-catalyzed hydrolysis of chloropentaphenylcyclotriphos phonitrile", Inorganic Chemistry, (1968), 7 (11), eq. 3,4, Experimental Section, pp. 2189-2192.

*Primary Examiner*—Peter G. O'Sullivan
(74) *Attorney, Agent, or Firm*—Sughrue Mion, PLLC

(57) ABSTRACT

This invention relates to a novel ionic compound being low in a risk of combustion, and more particularly to an ionic compound represented by the following formula (I):

$$(NPR^1_2)_n \qquad (I)$$

[wherein $R^1$s are each independently a halogen element or a monovalent substituent, provided that at least one of $R^1$s is an ionic substituent represented by the following general formula (II):

$$-N^+R^2_3 X^- \qquad (II)$$

(wherein $R^2$s are independently a monovalent substituent or hydrogen, provided that at least one of $R^2$s is not hydrogen and $R^2$s may be bonded with each other to form a ring; and $X^-$ is a monovalent anion); and n is 3 to 15].

4 Claims, 10 Drawing Sheets

IONIC COMPOUND

TECHNICAL FIELD

This invention relates to a novel ionic compound.

BACKGROUND ART

Since a report of Wilkes et al. in 1992, an ionic liquid attracts attention as a substance which is a liquid at normal temperature and excellent in an ion conductivity. In the ionic liquid, a cation is bonded with an anion via an electrostatic attraction, the number of the ion carrier is very large, a viscosity is relatively low and thereby an ion mobility is high even at normal temperature, so that the ionic liquid has a very high ion conductivity. Further, the ionic liquid has a high boiling point and a very wide temperature range in which it can remain in a liquid state, because it consists of the cation and anion. Furthermore, the ionic liquid is low in a flammability and very excellent in a thermal stability, because it has little vapor pressure (see J. Electrochem. Soc., 144 (1997) 3881 and "Function Creation and Application of Ionic Liquid", N. T. S, (2004)).

The ionic liquid has these various merits, so that it is recently studied to apply to electrolytes for a non-aqueous electrolyte secondary battery and an electric double layer capacitor (see JP-A-2004-111294 and JP-A-2004-146346). In particular, when the ionic liquid is used in the electrolyte for the electric double layer capacitor, it also serves as an ion source for forming an electric double layer, so that there is also a merit that it is not necessary to add an additional supporting electrolyte.

DISCLOSURE OF THE INVENTION

However, the inventors have studied and discovered that the above-mentioned ionic liquid commonly includes an organic group in order to be in a liquid state at normal temperature and has a risk of combustion.

It is, therefore, an object of the invention to solve the above-mentioned problems of the conventional techniques and to provide a novel ionic compound being low in a risk of combustion.

The inventors have made various studies in order to achieve the above objects and discovered that a novel substance having a structure, wherein a primary, secondary or tertiary amine is bonded with a cyclic phosphazene compound, has an ionic characteristic and low risk of combustion, and as a result the invention has been accomplished.

That is, the ionic compound according to the invention is represented by the following general formula (I):

$(NPR^1_2)_n$           (I)

[wherein $R^1$s are independently a halogen element or a monovalent substituent, provided that at least one of $R^1$s is an ionic substituent represented by the following general formula (II):

$-N^+R^2_3X^-$           (II)

(wherein $R^2$s are independently a monovalent substituent or hydrogen, provided that at least one of $R^2$s is not hydrogen and $R^2$s may be bonded with each other to form a ring; and $X^-$ is a monovalent anion); and n is 3 to 15].

In a preferable embodiment of the ionic compound according to the invention, n in the general formula (I) is 3 or 4.

In the ionic compound according to the invention, it is preferable that at least one of $R^1$s in the general formula (I) is the ionic substituent represented by the general formula (II) and the other is fluorine.

According to the invention, there can be provided a novel ionic compound being low in a risk of combustion.

BEST MODE FOR CARRYING OUT THE INVENTION

Figure 1:
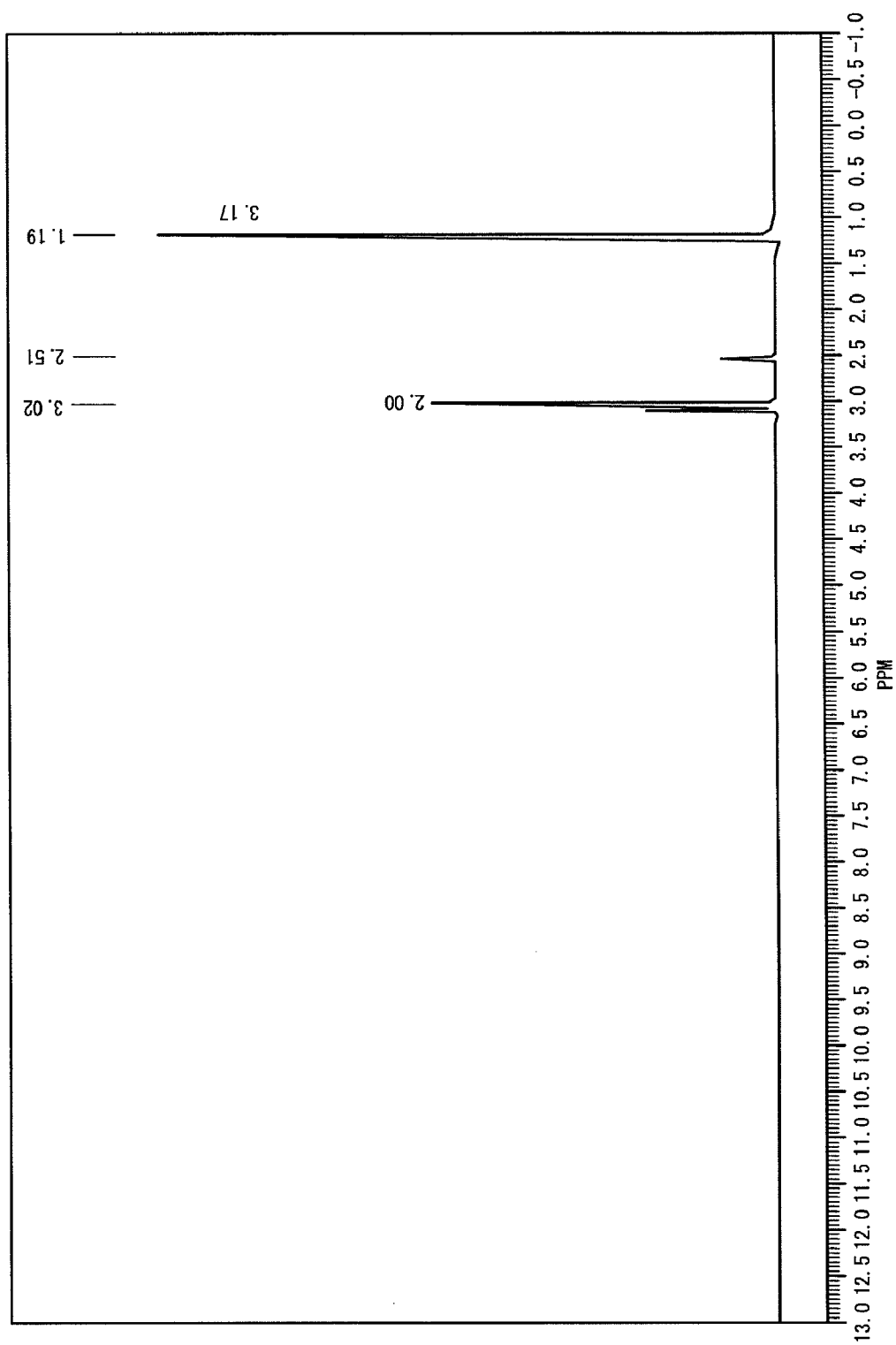
FIG. 1 is a result of $^1$H-NMR for a product obtained in the synthesis example 1.

The invention will be described in detail below. The ionic compound according to the invention is represented by the general formula (I). The compound of the formula (I) is a kind of a cyclic phosphazene compound having plural phosphorus-nitrogen double bonds and has an ionic characteristic, because at least one of $R^1$s is an ionic substituent of the formula (II). The ionic compound is decomposed to generate a nitrogen gas, a phosphate ester and the like during combustion, because it has a phosphazene skeleton. These nitrogen gas, phosphate ester and the like inhibit the combustion from progressing, so that the ionic compound has low risk of combustion. Further, when the ionic compound contains a halogen, the halogen acts as an active radical catching agent in an accidental combustion to decrease the risk of combustion. Furthermore, when the ionic compound contains an organic substituent, it has an effect of shielding oxygen because it forms a carbide (char) in the combustion.

In the general formula (I), $R^1$s are independently a halogen element or a monovalent substituent, provided that at least one of $R^1$s is an ionic substituent represented by the general formula (II). As the halogen element in $R^1$ are preferably mentioned fluorine, chlorine, bromine and the like. Among them, fluorine is particularly preferable. As the monovalent substituent in $R^1$ are mentioned an alkoxy group, an alkyl group, an aryloxy group, an aryl group, a carboxyl group, an acyl group and the like. As the alkoxy group are mentioned methoxy group, ethoxy group, methoxy ethoxy group, propoxy group, allyloxy group and vinyloxy group containing a double bond, an alkoxy-substituted alkoxy group such as methoxy ethoxy group, methoxy ethoxy ethoxy group or the like, and so on. As the alkyl group are mentioned methyl group, ethyl group, propyl group, butyl group, pentyl group and the like. As the aryloxy group are mentioned phenoxy group, methylphenoxy group, methoxy phenoxy group and the like. As the aryl group are mentioned phenyl group, tolyl group, naphthyl group and the like. As the acyl group are mentioned formyl group, acetyl group, propionyl group, butylyl group, isobutylyl group, valeryl group and the like. In these monovalent substituents, a hydrogen element is preferably substituted with a halogen element and as the halogen element are preferably mentioned fluorine, chlorine, bromine and the like.

In the general formula (I), n is 3 to 15, preferably 3 to 4, most preferably 3 in view of an availability of the starting material.

The ionic substituent represented by the general formula (II) is formed by bonding —$NR^2_3$ with X mainly through an electrostatic attraction. Therefore, the ionic compound of the formula (I) having the ionic substituent of the formula (II) has an ionic characteristic. Further, when it is in the liquid state, it becomes an ionic liquid, while when it is in the solid state, it becomes an ionic crystal.

In the general formula (II), $R^2$s are independently a monovalent substituent or hydrogen, provided that at least one of $R^2$s is not hydrogen and $R^2$s may be bonded with each other to form a ring. As the monovalent substituent in $R^2$ are mentioned an alkyl group, an aryl group and the like. As the alkyl group are mentioned methyl group, ethyl group, propyl group, butyl group, pentyl group and the like. As the aryl group are mentioned phenyl group, tolyl group, naphthyl group and the like. When the plural $R^2$s are bonded with each other to form a ring, as a ring formed by bonding any two of three $R^2$s are mentioned azacycloalkane rings such as an aziridine ring, an azetidine ring, a pyrrolidine ring, a piperidine ring and so on, and azacycloalkanone rings having a structure formed by substituting a methylene group in the azacycloalkane ring with a carbonyl group, and as a ring formed by bonding three $R^2$s are mentioned a pyridine ring and so on. In these monovalent substituents, a hydrogen element may be substituted with a halogen element or the like.

In the general formula (II), $X^-$ is a monovalent anion. As the monovalent anion in $X^-$ of the formula (II) are mentioned $F^-$, $Cl^-$, $Br^-$, $I^-$, $BF_4^-$, $PF_6^-$, $AsF_6^-$, $SbF_6^-$, $CF_3SO_3^-$, $(CF_3SO_2)_2N^-$, $(C_2F_5SO_2)_2N^-$, $(C_3F_7SO_2)_2N^-$, $(CF_3SO_2)(C_2F_5SO_2)N^-$, $(CF_3SO_2)(C_3F_7SO_2)N^-$, $(C_2F_5SO_2)(C_3F_7SO_2)N^-$ and so on.

In the ionic compound of the formula (I), at least one of $R^1$s is an ionic substituent represented by the general formula (II) and the other is preferable to be fluorine in view of the non-combustibility of the ionic compound.

The production method of the ionic compound according to the invention is not particularly limited. For example, a cyclic phosphazene compound represented by the following general formula (III):

$$(NPR^3_2)_n \quad \text{(III)}$$

[wherein $R^3$s are independently a halogen element or a monovalent substituent, provided that at least one of $R^3$s is chlorine; and n is 3 to 15] can be reacted with a primary, secondary or tertiary amine represented by the following general formula (IV):

$$NR^2_3 \quad \text{(IV)}$$

[wherein $R^2$s are the same meaning as mentioned above] to produce an ionic compound represented by the following general formula (V):

$$(NPR^4_2) \quad \text{(V)}$$

[wherein $R^4$s are independently a halogen element or a monovalent substituent, provided that at least one of $R^4$s is an ionic substituent represented by the following general formula (VI):

$$—N^+R^2_3Cl^- \quad \text{(VI)}$$

(wherein $R^2$s are the same meaning as mentioned above); and n is the same meaning as mentioned above] (that is, an ionic compound represented by the general formula (I) wherein $X^-$ in the formula (II) is $Cl^-$).

Further, the chlorine ion in the ionic compound represented by the general formula (V) can be substituted with another monovalent anion, if necessary. For example, the ionic compound represented by the general formula (V) can be reacted (subjected to an ion-exchange reaction) with a salt (ion-exchange agent) represented by the following general formula (VII):

$$A^+X^- \quad \text{(VII)}$$

[wherein $A^+$ is a monovalent cation and $X^-$ is a monovalent anion] to produce the ionic compound represented by the general formula (I).

Although the ionic compound represented by the general formula (V) can be produced by only mixing the cyclic phosphazene compound represented by the general formula (III) with the amine represented by the general formula (IV), the resulting ionic compound of the formula (V) may be unstable and hardly isolated. Therefore, it is preferable that the cyclic phosphazene compound represented by the general formula (III) and the amine represented by the general formula (IV) are added to a two-phase system composed of a water phase and an organic phase and reacted to produce the ionic compound represented by the general formula (V). In this method, the cyclic phosphazene compound of the formula (III) and the amine of the formula (IV) mainly exist in the organic phase, while the resulting ionic compound of the formula (V) mainly exists in the water phase because it has an ionic characteristic. Therefore, the water phase is separated from the organic phase and then the water in the water phase can be dried according to a known method to isolate the ionic compound of the formula (V), and the isolated ionic compound of the formula (V) stably exists under atmosphere. For an application wherein the ionic compound of the formula (V) can be used as an aqueous solution without isolation, the water phase containing the ionic compound of the formula (V) may be also used as it is.

In the general formula (III), $R^3$s are independently a halogen element or a monovalent substituent, provided that at least one of $R^3$s is chlorine. The amine of the formula (IV) is attached to the portion where $R^3$ in the formula (III) is chlorine. Therefore, the number of the ionic substituent represented by the formula (VI) and introduced into the ionic compound of the formula (V) can be controlled by adjusting the number of the chlorine bonded with the phosphorus in the skeleton of the cyclic phosphazene compound of the formula (III) as a starting material.

In the $R^3$ of the general formula (III), as the halogen element are preferably mentioned fluorine, bromine and the like as well as chlorine. Among them, chlorine and fluorine are particularly preferable. On the other hand, as the monovalent substituent in $R^3$ are mentioned the same ones as described in the section of the monovalent substituent in $R^1$. Further, n in the formula (III) is 3 to 15, preferably 3 to 4, most preferably 3 in view of an availability.

The cyclic phosphazene compound represented by the general formula (III) can be synthesized, for example, by a method wherein a commercially available phosphazene compound in which all $R^3$s in the formula (III) are chlorine is used as a starting material and all chlorines are fluorinated with a fluorinating agent and then an alkoxy group, an amine group or the like is introduced into a target position to be substituted with chlorine and thereafter the chlorination is again conducted with a chlorinating agent such as HCl, phosgene or the like, a method wherein after equivalent weight of fluorine to be introduced into the commercial phosphazene compound in which all $R^3$s in the formula (III) are chlorine is calculated, a necessary amount of a fluorinating agent is added, and so on. The number of the chlorine in the $R^3$s of the formula (III) can be controlled by varying the amount of the chlorinating agent used during the rechlorination or the fluorinating agent used during the fluorination or reaction conditions.

In the general formula (IV), $R^2$s have the same meaning as $R^2$s in the general formula (II) and are independently a monovalent substituent or hydrogen, provided that at least one of $R^2$s is not hydrogen and $R^2$s may be bonded with each other to form a ring. As the monovalent substituent in $R^2$ of the formula (IV) are mentioned the same ones as described in the section of the monovalent substituent in $R^2$ of the formula (II). As a ring formed by bonding any two of three $R^2$s and a ring formed by bonding three $R^2$s in the formula (IV) are mentioned the same ones as described in the section of the ring formed by bonding any two of three $R^2$s and the ring formed by bonding three $R^2$s in the formula (II). As the amine represented by the formula (IV) are concretely mentioned aliphatic tertiary amines such as trimethylamine, triethylamine, tripropylamine, tributylamine and so on, cyclic tertiary amines such as N-methyl-2-pyrrolidone, N-ethyl-2-pyrrolidone and so on, aromatic tertiary amines such as dialkyl-substituted anilines including dimethylaniline, pyridine and so on, aromatic primary amines such as aniline and so on. Among them, the tertiary amines are preferable.

In the general formula (V), $R^4$s are independently a halogen element or a monovalent substituent, provided that at least one of $R^4$s is an ionic substituent represented by the general formula (VI). As the halogen element in $R^4$ are mentioned fluorine, chlorine, bromine and so on. A part of $R^4$s can be chlorine by adjusting the amount of the amine of the formula (IV) used or the like. On the other hand, as the monovalent substituent in $R^4$ are mentioned the same ones as described in the section of the monovalent substituent in $R^1$. Further, n in the formula (V) is 3 to 15, preferably 3 to 4, most preferably 3 in view of an availability of the starting material.

In the general formula (VI), $R^2$s have the same meaning as $R^2$s in the general formula (II) and are independently a monovalent substituent or hydrogen, provided that at least one of $R^2$s is not hydrogen and $R^2$s may be bonded with each other to form a ring. As the monovalent substituent in $R^2$ of the formula (VI) are mentioned the same ones as described in the section of the monovalent substituent in $R^2$ of the formula (II). As a ring formed by bonding any two of three $R^2$s and a ring formed by bonding three $R^2$s in the formula (VI) are mentioned the same ones as described in the section of the ring formed by bonding any two of three $R^2$s and the ring formed by bonding three $R^2$s in the formula (II).

In the production of the ionic compound of the formula (V), the amount of the amine of the formula (IV) used can be properly selected depending on the target amount of the amine introduced and, for example, it is preferably within a range of 1 to 2.4 mol per 1 mol of chlorine in $R^3$ of the cyclic phosphazene compound of the formula (III).

The reaction temperature during the reaction of the cyclic phosphazene compound of the formula (III) with the amine of the formula (IV) is not particularly limited, but is preferably within a range of 20° C. to 80° C. and the reaction sufficiently progresses at room temperature. Also, the reaction pressure is not particularly limited, and the reaction can be carried out under atmospheric pressure.

In the two-phase system composed of the water phase and the organic phase, as an organic solvent used in the organic phase is preferable one not having a miscibility with water and capable of dissolving the cyclic phosphazene compound of the formula (III) and the amine of the formula (IV) and concretely low-polar solvents such as chloroform, toluene and so on are preferable. The amounts of the water phase and the organic phase used are not particularly limited, but the volume of the water phase is preferably within a range of 0.2 to 5 mL per 1 mL of the cyclic phosphazene compound of the formula (III) and the volume of the organic phase is preferably within a range of 2 to 5 mL per 1 mL of the cyclic phosphazene compound of the formula (III).

In the general formula (VII), $A^+$ is a monovalent cation and $X^-$ is a monovalent anion. As the monovalent cation in $A^+$ of the formula (VII) are mentioned $Ag^+$, $Li^+$ and so on. As the monovalent anion in $X^-$ of the formula (VII) are mentioned monovalent anions except $Cl^-$ and are concretely mentioned $BF_4^-$, $PF_6^-$, $AsF_6^-$, $SbF_6^-$ and $CF_3SO_3^{31}$, as well as imide ions such as $(CF_3SO_2)_2N^-$, $(C_2F_5SO_2)_2N^-$, $(C_3F_7SO_2)_2N^-$, $(CF_3SO_2)(C_2F_5SO_2)N^-$, $(CF_3SO_2)(C_3F_7SO_2)N^-$, $(C_2F_5SO_2)(C_3F_7SO_2)N^-$ and so on. When $A^+$ is $Li^+$, the imide ions are preferable as $X^-$. This is because the imide ion has a large ionic radius as contrasted with $Li^+$ having a small ionic radius and thereby it is well reacted due to a difference in the ionic radius between the cation and the anion (hard/soft-acid/base principle) and a substitution reaction progresses well. On the other hand, when $A^+$ is $Ag^+$, almost every anion can be used. When $Ag^+X^-$ is used as the salt of the formula (VII), AgCl settles out so that it is also easy to remove impurity.

In the production of the ionic compound of the formula (I), the amount of the salt of the formula (VII) used can be properly selected depending on the target amount of the chlorine ion in the ionic compound of the formula (V) and, for example, it is preferably within a range of 1 to 1.5 mol per 1 mol of the chlorine ion in the ionic compound of the formula (V).

Further, the reaction temperature during the reaction of the ionic compound of the formula (V) with the salt of the formula (VII) is not particularly limited, but is preferably within a range of room temperature to 50° C. and the reaction sufficiently progresses at room temperature. Also, the reaction pressure is not particularly limited, and the reaction can be carried out under atmospheric pressure.

The reaction of the ionic compound of the formula (V) with the salt of the formula (VII) is preferably carried out in a water phase. When the ionic compound of the formula (V) is reacted with a silver salt represented by the formula (VII) wherein $A^+$ is $Ag^+$, silver chloride is produced as a by-product and the silver chloride has a very low solubility in water. Therefore, when the reaction is carried out in the water phase, it is easy to remove the by-product. The volume of the water phase is not particularly limited, but is preferably within a range of 2 to 5 mL per 1 mL of the ionic compound of the formula (V).

The production method of the ionic compound of the formula (I) is commonly carried out in the water phase. When the ionic compound of the formula (I) is isolated from the water phase, the water in the water phase is evaporated according to a known method. For an application wherein the ionic compound of the formula (I) can be used as an aqueous solution without isolation, the water phase containing the ionic compound of the formula (I) may be also used as it is.

When the above-mentioned ionic compound according to the invention is in a liquid state at room temperature (25° C.), it can be used as an electrolyte for an electric double layer capacitor, an electrolyte for a lithium-ion battery, an electrolyte for a dye-sensitized solar cell, a reaction solvent for an organic synthesis, an extracting solvent for an organic compound and a magnetic fluid, while when it is in a solid state at room temperature (25° C.), it can be used as a salt. It has a high non-combustibility in both of the liquid and solid states and can significantly suppress the risk of combustion in the application.

EXAMPLES

The following examples are given in illustration of the invention and are not intended as limitations thereof.

Synthesis Example 1

Figure 2:
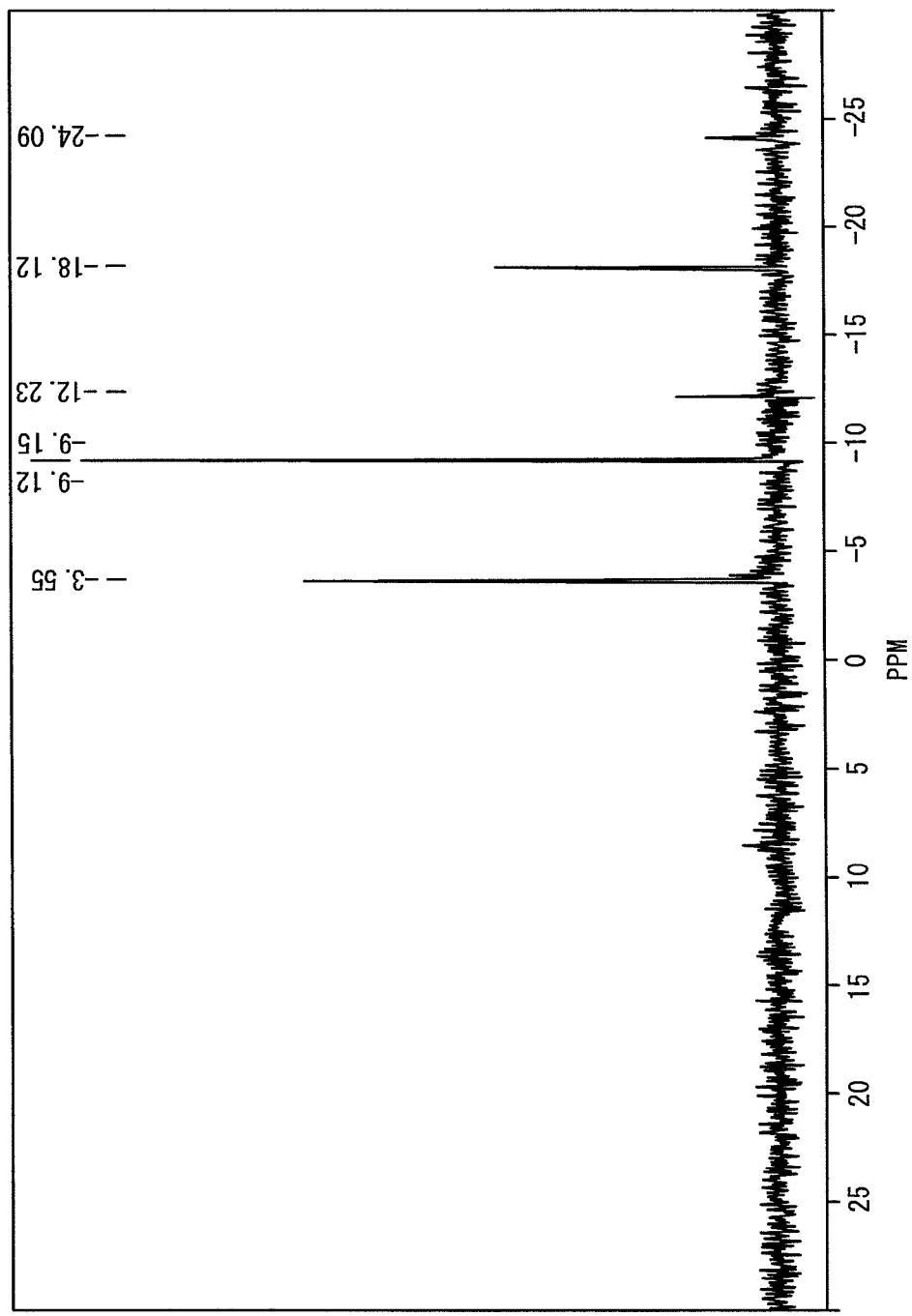
FIG. 2 is a result of $^{31}$P-NMR for the product obtained in the synthesis example 1.

A two-phase system composed of 5 g of water and 5 g of chloroform is prepared, and to the two-phase system are sequentially added dropwise 5 mL of triethylamine and 5 mL of a cyclic phosphazene compound represented by the general formula (III) wherein n is 3, one of six $R^3$s is chlorine and five thereof are fluorine. The two-phase system is stirred with a stirrer and then heat generation is observed along with a reaction. After stirring for 3 minutes, a water phase is collected and water is evaporated to produce a white crystal. It is further dried under a reduced pressure to obtain 0.2 g of a white crystal (yield: 53%). The resulting white crystal is insoluble in chloroform, methanol and acetonitrile, but soluble in water. The resulting white crystal is dissolved in deuterium oxide and analyzed by $^1$H-NMR to confirm that the white crystal is represented by the general formula (I) wherein n is 3, five of six $R^1$s are fluorine and one thereof is —N$^+$(CH$_2$CH$_3$)$_3$Cl$^-$. The result of $^1$H-NMR for the product is shown in FIG. 1, the result of $^{31}$P-NMR for the product is shown in FIG. 2 and the reaction scheme is shown below.

Reaction scheme 1

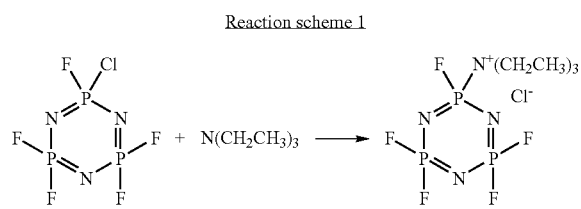

Synthesis Example 2

Figure 3:
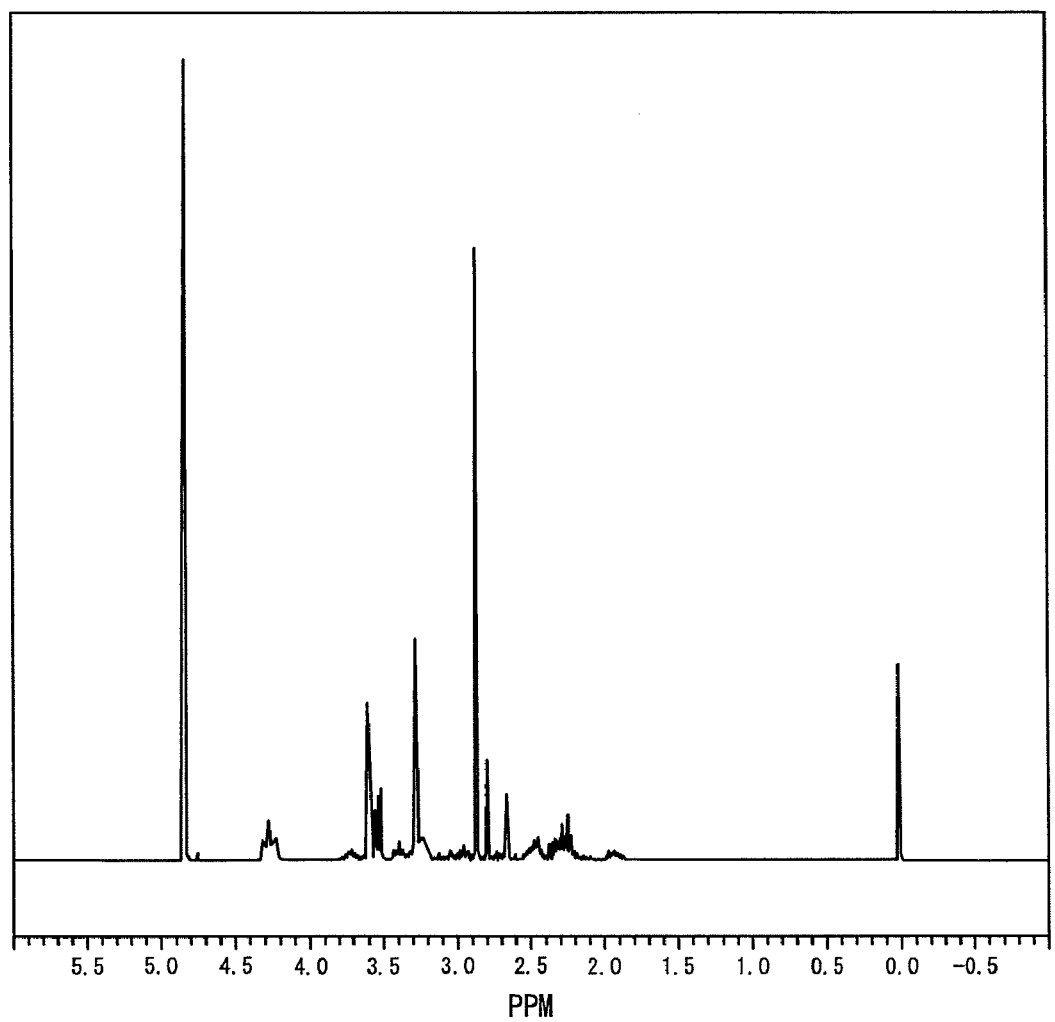
FIG. 3 is a result of $^1$H-NMR for a product obtained in the synthesis example 2.
Figure 4:
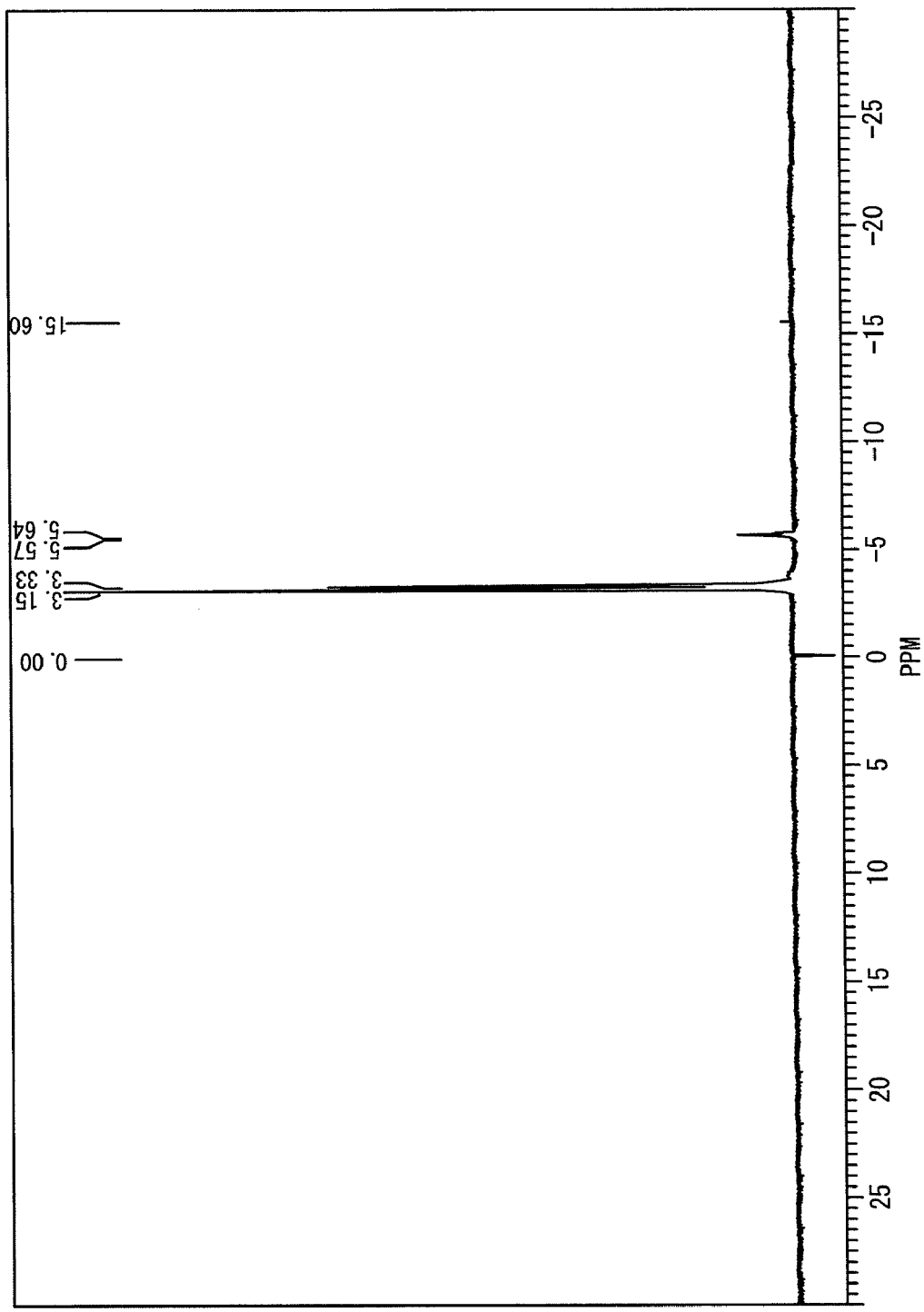
FIG. 4 is a result of $^{31}$P-NMR for the product obtained in the synthesis example 2.

A two-phase system composed of 15 mL of water and 15 mL of chloroform is prepared, and to the two-phase system are sequentially added dropwise 5 mL of N-methyl-2-pyrrolidone and 5 mL of a cyclic phosphazene compound represented by the general formula (III) wherein n is 3, one of six $R^3$s is chlorine and five thereof are fluorine. The two-phase system is then stirred with cooling and as a result, a white crystal is precipitated in a chloroform phase. It is warmed to room temperature and stirred, and thereby the white crystal disappears. The chloroform phase was colorless before the reaction but becomes clouded after the reaction. A water phase is collected by using a pipette and evaporated, and then water is distilled away by using a vacuum pump to obtain 5.1 g of a white crystal (yield: 74%). The resulting white crystal is dissolved in deuterium oxide and analyzed by $^1$H-NMR to confirm that the white crystal is an ionic compound represented by the general formula (I) wherein n is 3, five of six $R^1$s are fluorine and one thereof is the ionic substituent represented by the general formula (II) wherein X$^-$ is Cl$^-$, one of $R^2$s is methyl group, the other two $R^2$s are bonded with each other to form 2-azacyclopentanone ring with a nitrogen atom. The result of $^1$H-NMR for the product is shown in FIG. 3, the result of $^{31}$P-NMR for the product is shown in FIG. 4 and the reaction scheme is shown below.

Reaction scheme 2

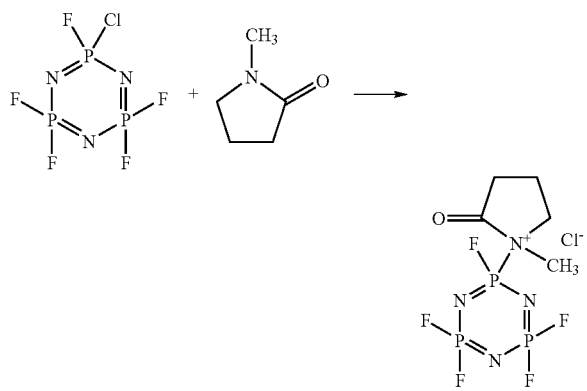

Synthesis Example 3

Figure 5:
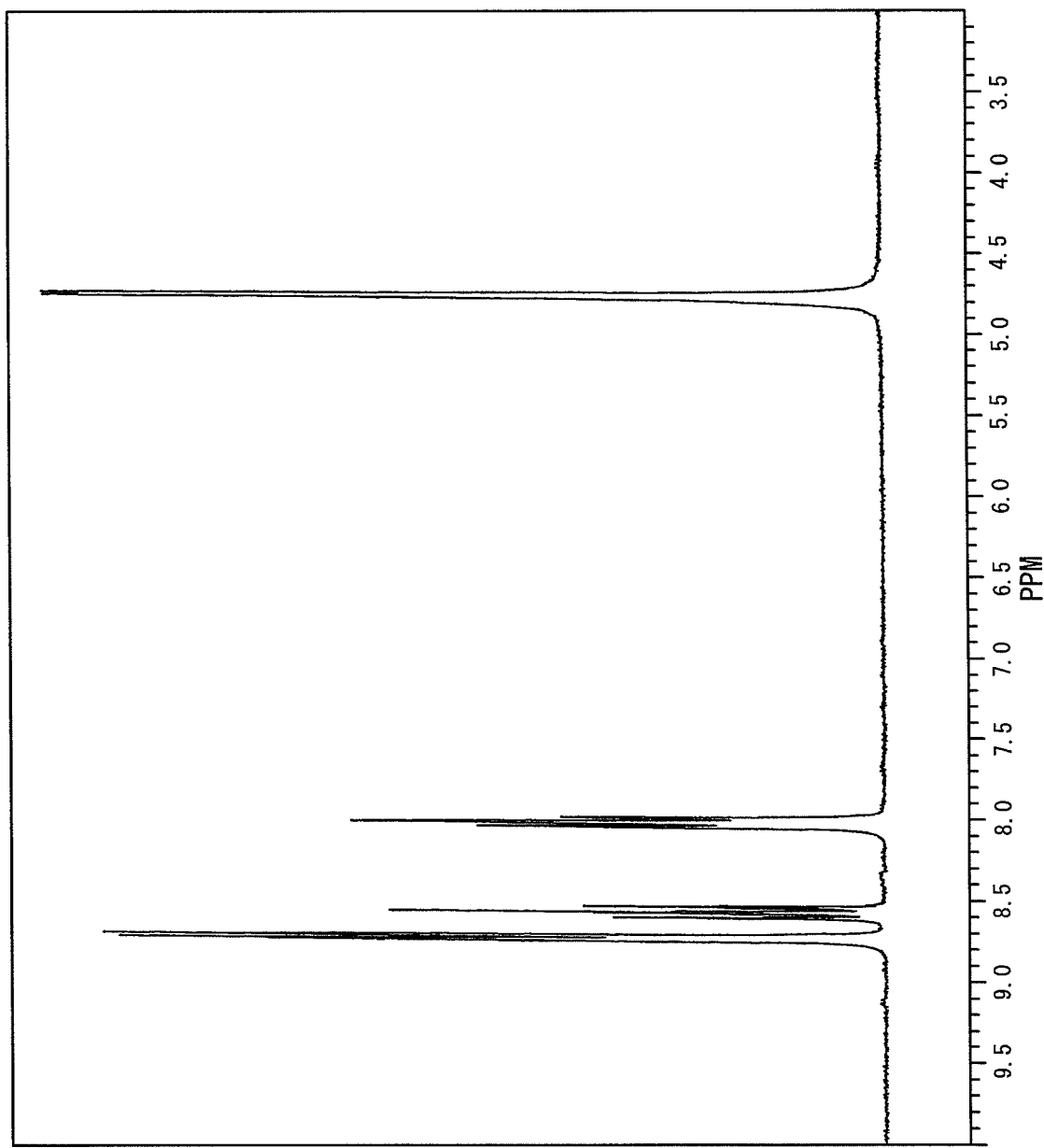
FIG. 5 is a result of $^1$H-NMR for a product obtained in the synthesis example 3.
Figure 6:
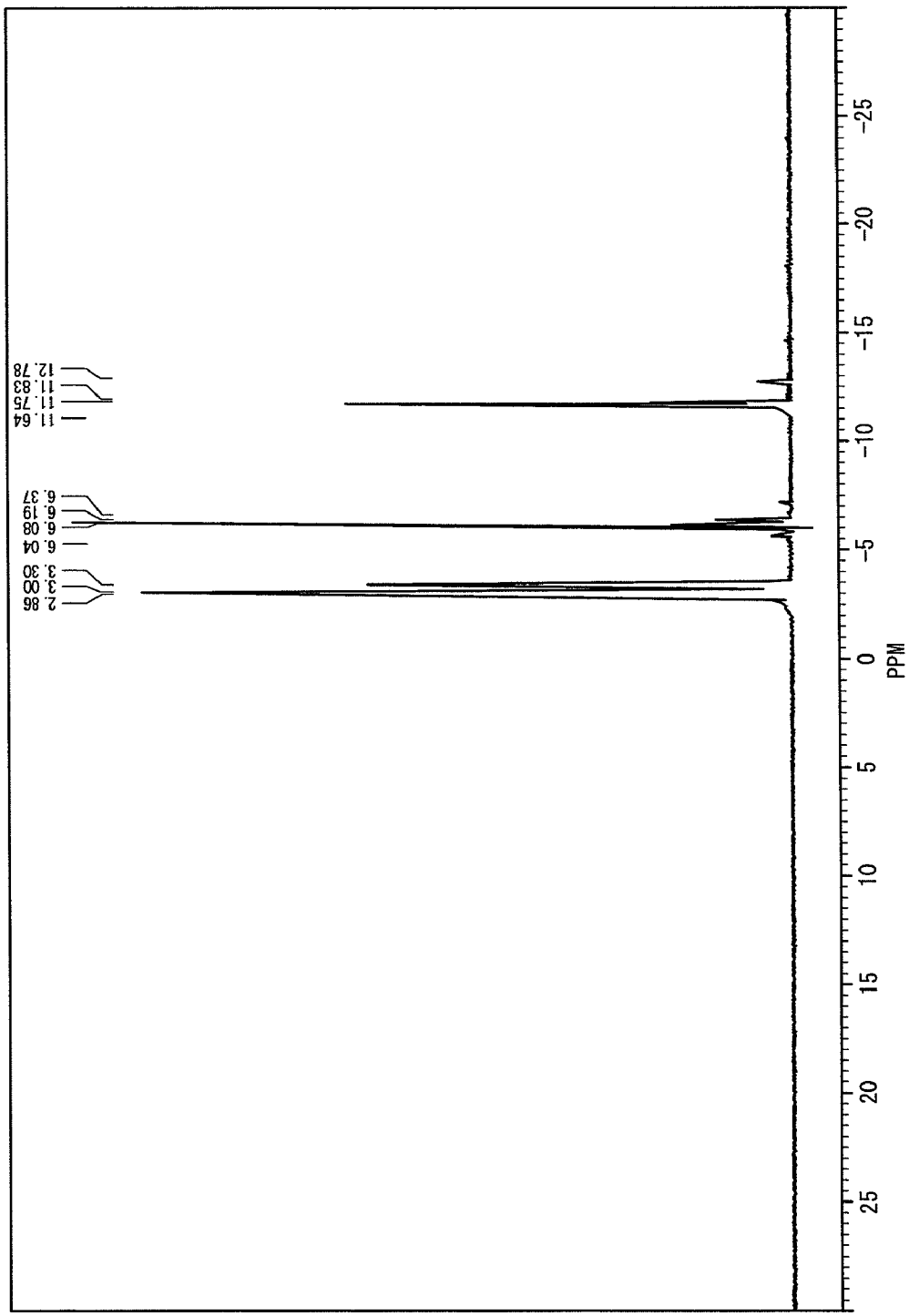
FIG. 6 is a result of $^{31}$P-NMR for the product obtained in the synthesis example 3.

A two-phase system composed of 15 mL of water and 15 mL of chloroform is prepared, and to the two-phase system are sequentially added dropwise 5 mL of pyridine and 5 mL of a cyclic phosphazene compound represented by the general formula (III) wherein n is 3, one of six $R^3$s is chlorine and five thereof are fluorine. The two-phase system is then stirred with cooling and as a result, a white crystal is precipitated in a chloroform phase. It is warmed to room temperature and stirred, and thereby the white crystal disappears. The chloroform phase was colorless before the reaction but becomes clouded after the reaction. A water phase is collected by using a pipette and evaporated, and then water is distilled away by using a vacuum pump to obtain 5.2 g of a white crystal (yield: 57%). The resulting white crystal is dissolved in deuterium oxide and analyzed by $^1$H-NMR to confirm that the white crystal is represented by the general formula (I) wherein n is 3, five of six $R^1$s are fluorine and one thereof is —N+C$_5$H$_5$Cl$^-$. The result of $^1$H-NMR for the product is shown in FIG. 5, the result of $^{31}$P-NMR for the product is shown in FIG. 6 and the reaction scheme is shown below.

Reaction scheme 3

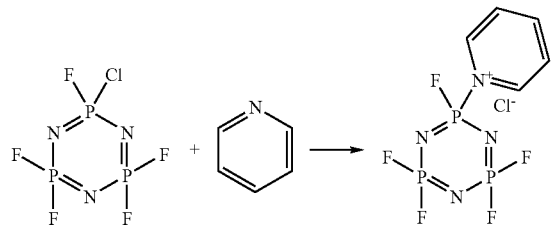

Synthesis Example 4

Figure 7:
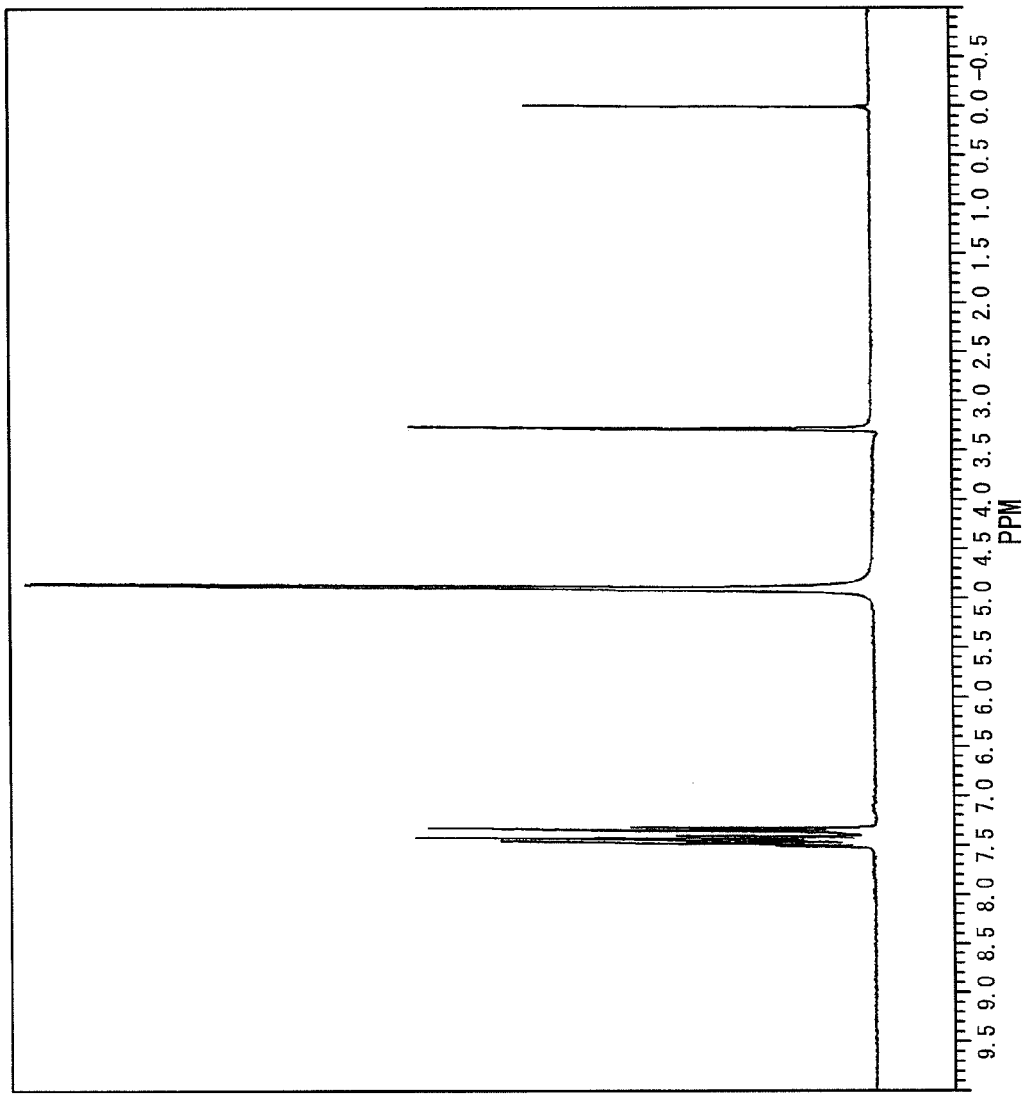
FIG. 7 is a result of $^1$H-NMR for a product obtained in the synthesis example 4.
Figure 8:
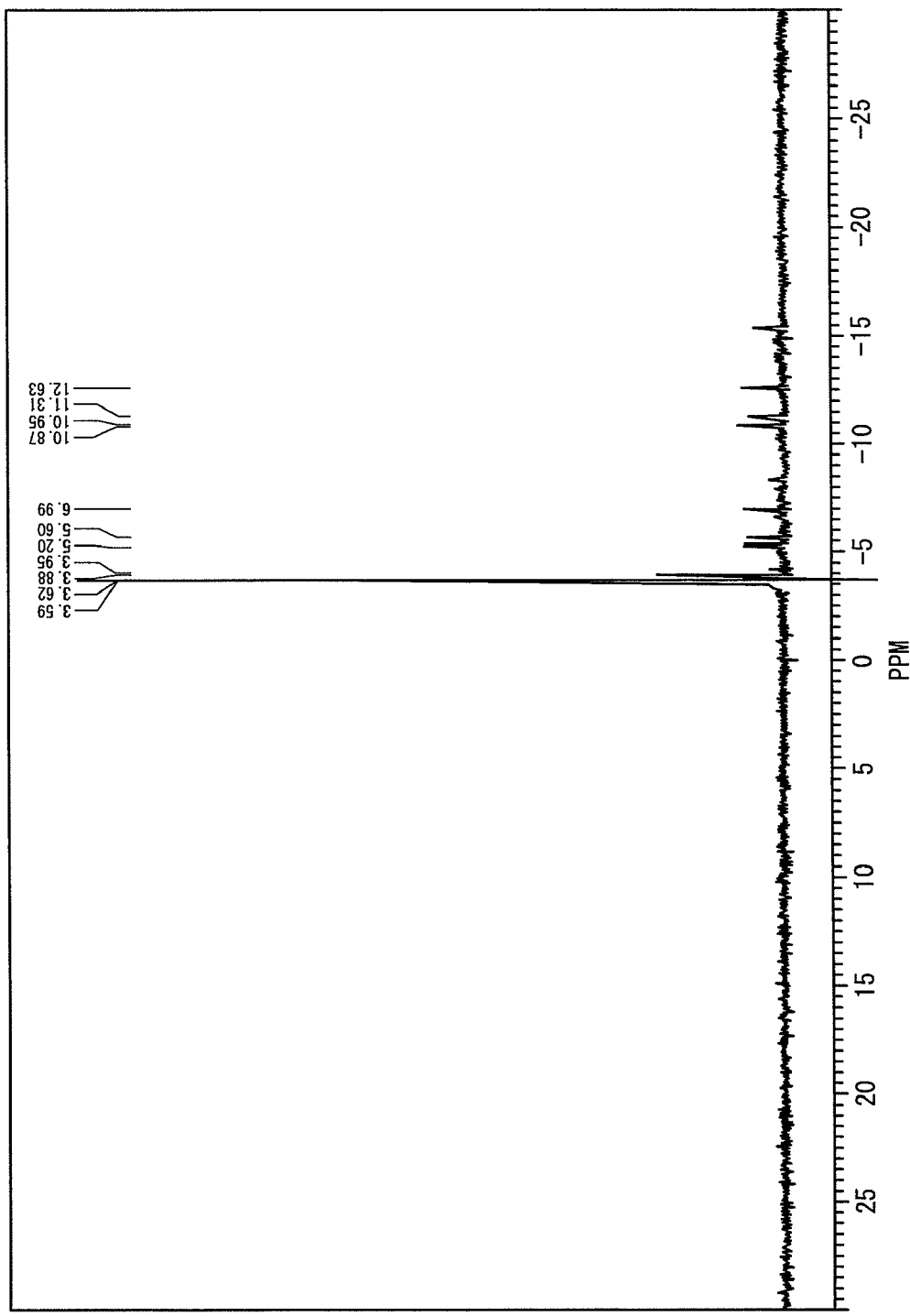
FIG. 8 is a result of $^{31}$P-NMR for the product obtained in the synthesis example 4.

A two-phase system composed of 15 mL of water and 15 mL of chloroform is prepared, and to the two-phase system are sequentially added dropwise 5 mL of aniline and 5 mL of a cyclic phosphazene compound represented by the general formula (III) wherein n is 3, one of six $R^3$s is chlorine and five thereof are fluorine. The two-phase system is then stirred with cooling and as a result, a white crystal is precipitated in a chloroform phase. It is warmed to room temperature and stirred, and thereby the white crystal disappears. The chloroform phase was colorless before the reaction but becomes clouded after the reaction. A water phase is collected by using a pipette and evaporated, and then water is distilled away by using a vacuum pump to obtain 4.8 g of a white crystal (yield: 54%). The resulting white crystal is dissolved in deuterium oxide and analyzed by $^1$H-NMR to confirm that the white crystal is represented by the general formula (I) wherein n is 3, five of six $R^1$s are fluorine and one thereof is —$N^+H_2C_6H_5Cl^-$. The result of $^1$H-NMR for the product is shown in FIG. 7, the result of $^{31}$P-NMR for the product is shown in FIG. 8 and the reaction scheme is shown below.

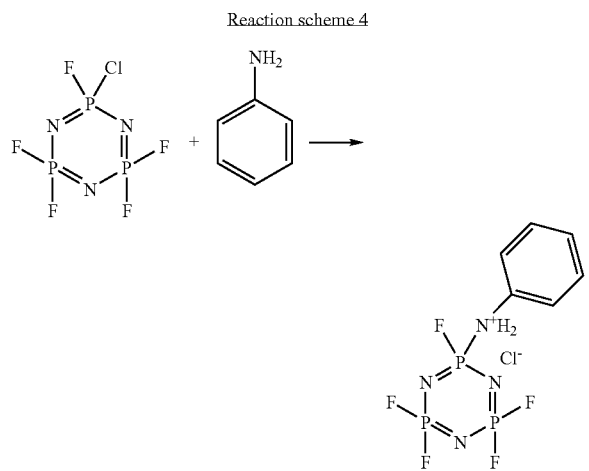

Synthesis Example 5

Figure 9:
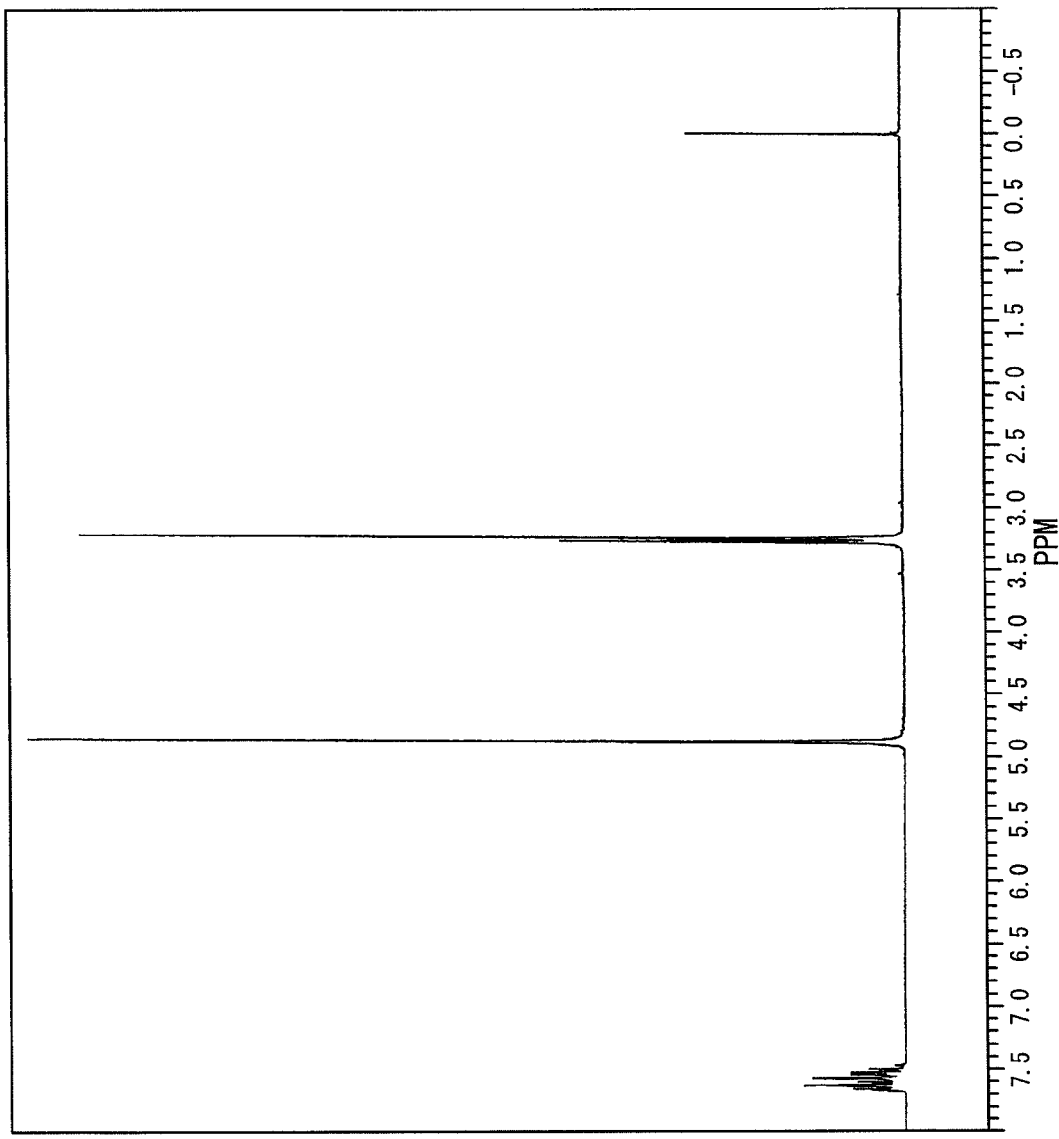
FIG. 9 is a result of $^1$H-NMR for a product obtained in the synthesis example 5.
Figure 10:
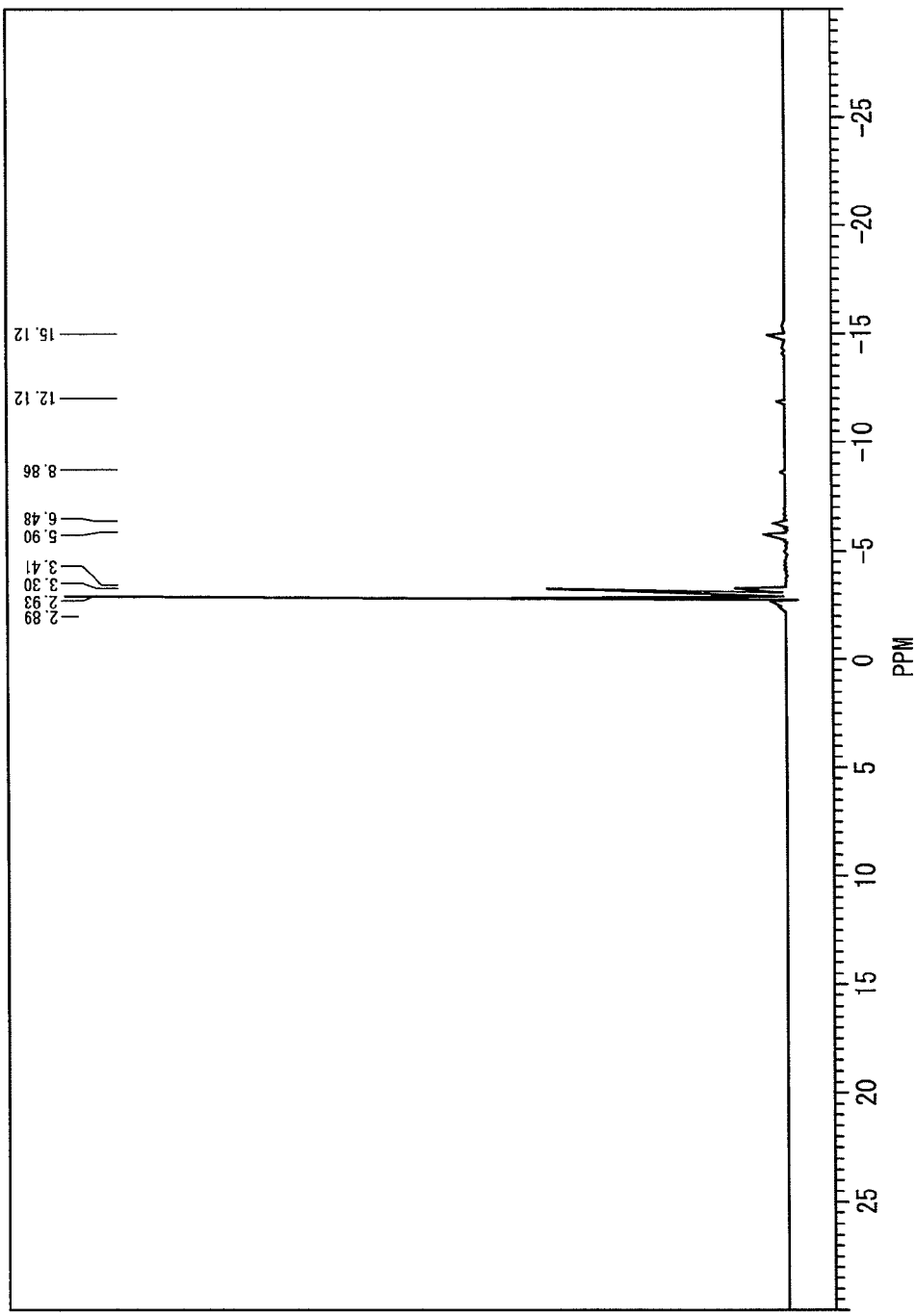
FIG. 10 is a result of $^{31}$P-NMR for the product obtained in the synthesis example 5.

A two-phase system composed of 15 mL of water and 15 mL of chloroform is prepared, and to the two-phase system are sequentially added dropwise 5 mL of dimethylaniline and 5 mL of a cyclic phosphazene compound represented by the general formula (III) wherein n is 3, one of six $R^3$s is chlorine and five thereof are fluorine. The two-phase system is then stirred with cooling and as a result, a white crystal is precipitated in a chloroform phase. It is warmed to room temperature and stirred, and thereby the white crystal disappears. The chloroform phase was colorless before the reaction but becomes clouded after the reaction. A water phase is collected by using a pipette and evaporated, and then water is distilled away by using a vacuum pump to obtain 5.1 g of a white crystal (yield: 52%). The resulting white crystal is dissolved in deuterium oxide and analyzed by $^1$H-NMR to confirm that the white crystal is represented by the general formula (I) wherein n is 3, five of six $R^1$s are fluorine and one thereof is —$N^+(CH_3)_2C_6H_5Cl^-$. The result of $^1$H-NMR for the product is shown in FIG. 9, the result of $^{31}$P-NMR for the product is shown in FIG. 10 and the reaction scheme is shown below.

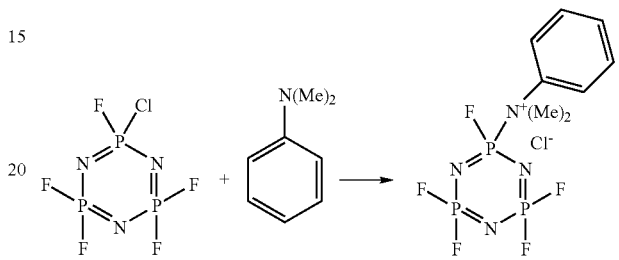

INDUSTRIAL APPLICABILITY

The ionic compound according to the invention can be used as an electrolyte for an electric double layer capacitor, an electrolyte for a lithium-ion battery, an electrolyte for a dye-sensitized solar cell, a reaction solvent for an organic synthesis, an extracting solvent for an organic compound and a magnetic fluid.

The invention claimed is:

1. An ionic compound represented by the following general formula (I):

$$(NPR^1{}_2)_n \quad (I)$$

[wherein $R^1$s are independently fluorine or an ionic substituent represented by the following general formula (II):

$$-N^+R^2{}_3X^- \quad (II)$$

(wherein $R^2$s are independently a monovalent substituent or hydrogen, provided that at least one of $R^2$s is not hydrogen and $R^2$s may be bonded with each other to form a ring; and $X^-$ is a monovalent anion), provided that at least one of R1s is the ionic substituent represented by the general formula (II) and at least one of R1s is fluorine; and n is 3 to 15].

2. An ionic compound according to claim 1, wherein n in the general formula (I) is 3 or 4.

3. An ionic compound according to claim 1, which is a liquid at 25° C.

4. An ionic compound according to claim 1, which is a solid at 25° C.

\* \* \* \* \*